United States Patent [19]
Frassetti

[11] Patent Number: 5,116,351
[45] Date of Patent: May 26, 1992

[54] SAFETY SCALPEL

[76] Inventor: Paris R. Frassetti, 1378 Dahill Rd., Brooklyn, N.Y. 11204

[21] Appl. No.: 419,782

[22] Filed: Oct. 11, 1989

[51] Int. Cl.⁵ .............................................. A61B 17/32
[52] U.S. Cl. ..................................... 606/167; 30/161; 30/286
[58] Field of Search ................. 606/167, 172; 30/331, 30/2, 157, 286, 295, 161

[56] References Cited

U.S. PATENT DOCUMENTS

| | | | |
|---|---|---|---|
| 2,209,751 | 7/1940 | Wulff | 30/2 X |
| 2,215,216 | 9/1940 | Gits et al. | 30/2 |
| 2,889,623 | 6/1959 | Baker | 30/2 |
| 3,002,273 | 10/1961 | Merritt | 30/2 |
| 3,641,667 | 2/1972 | Leopoldi | 30/2 |
| 3,868,774 | 3/1975 | Miori | 30/161 |
| 3,930,309 | 1/1976 | Collins | 30/161 |
| 4,683,656 | 8/1987 | Peyrot et al. | 30/2 X |
| 4,713,885 | 12/1987 | Keklak et al. | 30/2 X |
| 4,868,985 | 9/1989 | Rehm | 30/2 X |

Primary Examiner—Michael H. Thaler
Attorney, Agent, or Firm—James & Franklin

[57] ABSTRACT

The scalpel includes a handle with a blade moveably mounted to it by a leaf spring. A blade protecting sheath is fixably mounted to the handle. In its normal position, the blade is within the sheath such that the cutting edge is protected. In order to expose the cutting edge, the blade is depressed against the force of the spring. When not in use, the blade may be locked within the sheath.

1 Claim, 2 Drawing Sheets

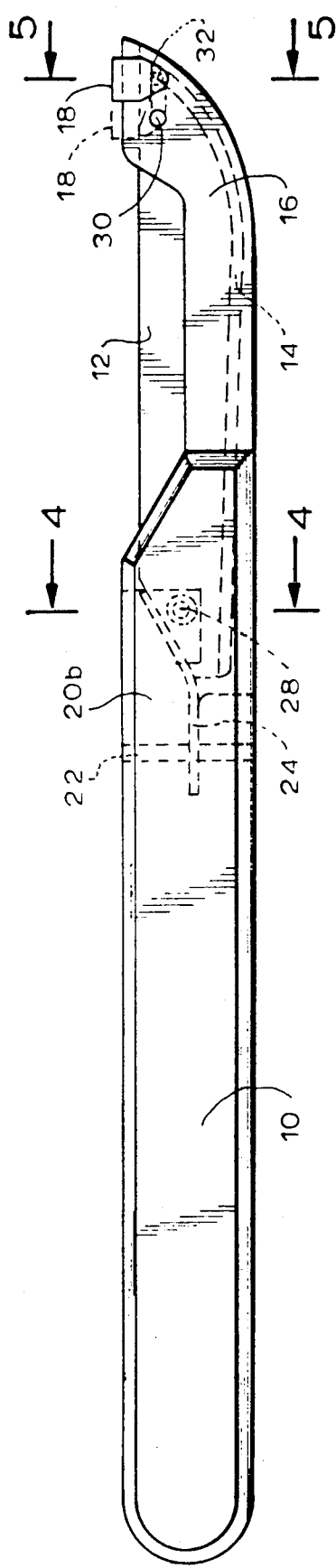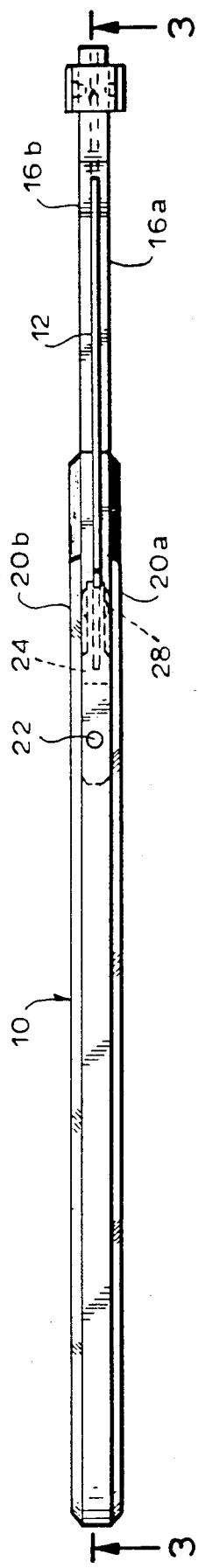

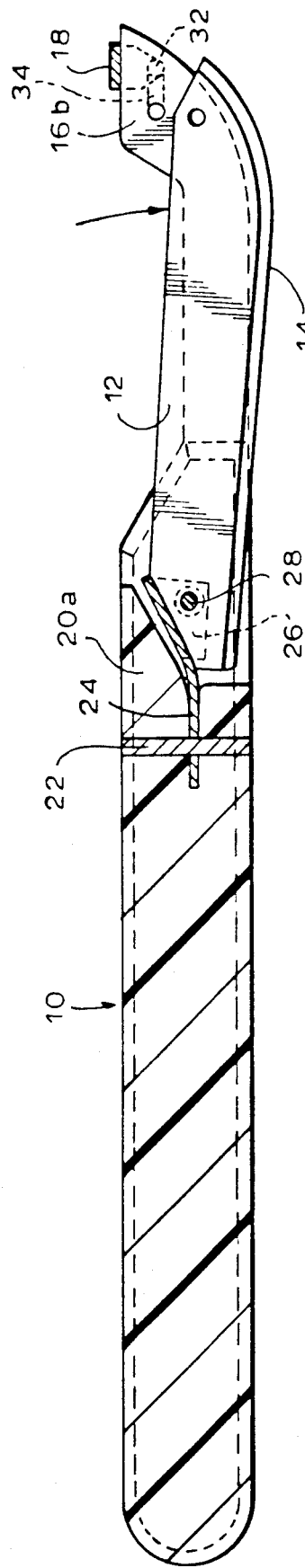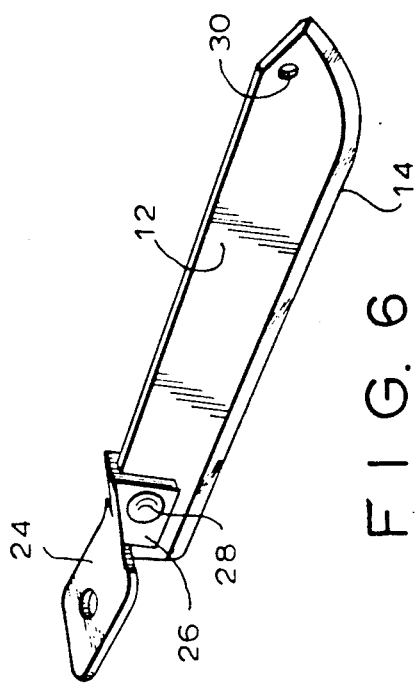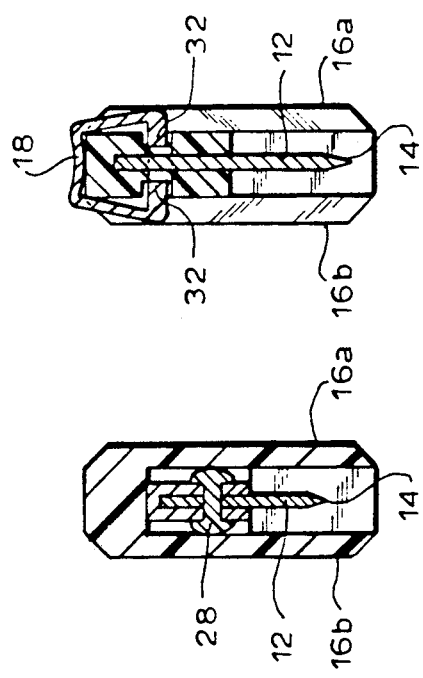

SAFETY SCALPEL

The present invention relates to scalpels and similar devices including blades with cutting edges and more particularly to a safety scalpel in which the blade must be depressed against the force of a spring to expose the cutting edge and which may be locked in the protected position.

Scalpels and similar types of cutting instruments which include blades with sharp cutting edges are used by medical personnel and other individuals for surgical procedures, autopsies, dissections and the like. Conventional scalpels used for this purpose have a stationary blade with a very sharp cutting edge. The edge is always exposed and hence creates a hazard not only to the individuals using the scalpel and their support staff but to anyone who may come in contact with the instrument. Not only is such an exposed cutting edge a hazard because it can cause a severe cut but also because the cutting edge may be contaminated with various infectious viruses which can be transmitted even by means of a small cut or nick.

The present invention relates to a very simple, inexpensive structure which protects the cutting edge from exposure in its normal position and requires depression of the blade against the force of a spring relative to a fixedly mounted sheath in order to expose the cutting edge. The blade is spring loaded towards the protected position such that when the depressive force is removed, the blade would automatically move back to its protected position. A locking device is incorporated in the structure to prevent accidental depression of the blade and hence exposure of the cutting edge.

It is, therefore, a prime object of the present invention to provide a safety scalpel which includes a blade with a cutting edge which is normally protected from exposure.

It is another object of the present invention to provide a safety scalpel which requires depression of the blade against the force of a spring in order to expose the cutting edge.

It is another object of the present invention to provide a safety scalpel which includes a device for locking the blade in the protected position.

It is another object of the present invention to provide a safety scalpel made of simple expensive parts which function reliably together.

In accordance with the present invention, a scalpel is provided comprising a handle, a blade with a cutting edge and means for protecting the cutting edge from exposure. Means are providing for mounting the blade and the protecting means to the handle for relative movement between a position in which the cutting edge is protected and the position wherein the cutting edge is exposed. Means are provided for biasing the mounting means towards the protected position.

In addition, means are provided for locking the blade and the protecting means in the protected position. In this manner, the blade cannot accidentally be moved towards the exposed position.

The protecting means is preferably mounted in a fixed position relative to the handle. Preferably, the protective means in the form of a sheath.

The mounting means preferably comprises leaf spring means operably connecting the blade to the handle. The blade must be moved against the bias of the spring means in order to expose the cutting edge.

The protecting means preferably comprises a planar element situated in substantially parallel spaced relation with the blade. The elements has an edge which overlaps the cutting edge to protect the cutting edge when the blade and the protecting means are in the protected position.

The protecting means most preferably comprises a pair of spaced planar elements substantially parallel with the blade and situated on either side thereof. At least one of the element has an edge which overlaps the cutting edge of the blade to protect the cutting edge when the blade and the protecting means are in the protected position.

A non-cutting edge portion of the blade is accessible when the blade and the protecting means are in the protected position. The accessible portion may be depressed to move the blade towards the exposed position.

A cut-away section of the protective means is provided for exposing the accessible blade portion. It is the cut-away section which provides clearance for the finger to permit the blade to be depressed.

The locking means comprises means for preventing relative movement between the blade and the protecting means. The locking means preferably comprises a recess on the blade and a part having a protrusion. The part is mounted for movement on the protecting means from a first position wherein the protrusion is situated with the recess and a second position wherein the protrusion is remote from the recess.

To these and such other object which may hereinafter appear the present invention relates to a safety scalpel as described in detail in the following specification and recited in the annexed claims, taken together with the accompanying drawings where like numerals refer to like parts and in which:

FIG. 1 is a side elevational view of the safety scalpel of the present invention;

FIG. 2 is a top elevational view of the safety scalpel of the present invention;

FIG. 3 is a cross-sectional view taken along line 3—3 of FIG. 2;

FIG. 4 is a cross-sectional view taken along line 4—4 of FIG. 1;

FIG. 5 is a cross-sectional view taken along line 5—5 of FIG. 1; and

FIG. 6 is an isometric view of the blade and leaf spring of the present invention.

As shown in the drawings, the safety scalpel of the present invention includes a handle section, generally designated 10, a blade 12 with a cutting edge 14, a protective sheath 16 and locking means 18. Handle 10 has a hollow section 20 which is formed by walls 20a and 20b which are spaced a short distance from each other. A shaft 22 situated between walls 20a and 20b extends from the top edge to the bottom edge of handle 10. Mounted on shaft 22 is leaf spring 24 which in turn carries blade 12. Accordingly, blade 12 is moveably mounted with respect to handle 10 by leaf spring 24. Blade 12 is mounted to a bifuricated portion 26 of leaf spring 24 by means of a pin or shaft 28.

Sheath 16, within which blade 12 is mounted, extends from the forward end of handle 10 and is fixably mounted thereto. Blade 12 can move relative to sheath 16 between a protected position illustrated in FIG. 1 in which the cutting edge 12 is substantially within sheath 16, that is, the lower edge of the sheath overlaps cutting edge 12 such that it is protected and an exposed position, illustrated in FIG. 3, wherein blade 12 is moved relative to sheath 16 such that cutting edge 14 is exposed. It should be noted that the upper portion of sheath 16 is cut-away such that the top edge of blade 12 is accessible. This cut-away portion provides clearance for the finger to permit the accessible portion of blade 12 to be depressed to expose cutting edge 14. When the force applied to the blade is released, the blade will return to the protected position within the sheath due to the action of leaf spring 24.

As best seen in FIGS. 4 and 5, sheath 16 is itself bifurcated. It is made up of planar elements 16a and 16b which are substantially parallel to each other and spaced apart to permit blade 12 to be situated therebetween. The bottom edge of sheath 16 normally overlaps the cutting edge 14 of blade 12 when the blade is in the protected first position so as to protect the cutting edge.

In order to lock blade 12 in the protected position, a simple locking mechanism is provided. The locking mechanism includes an opening 30 in blade 12 and a part 18 moveably mounted on the top portion of sheath 16. Part 18, as best seen in FIG. 5, is slideably mounted on sheath 16 and has a pair of oppositely oriented inwardly extending protrusions 32 which, when part 18 is in its position closest to handle 10, align with and lodge within opening 30 to prevent relative movement between blade 12 and the sheath 16. However, when part 18 is moved in a direction away from handle 10 such that protrusions 32 move along slot 34 in the sheath 16 so that they are no longer in alignment with recess 30, the locking mechanism is released, permitting relative movement of blade 12 with respect to sheath 16.

It should now be appreciated that the present invention relates to a safety scalpel which includes a blade with a cutting edge which is moveably mounted with respect to a protective sheath. In its normal position, the sheath protects the cutting edge of the blade from exposure. The cutting edge may be exposed by depressing the blade relative to the sheath, against the force of the spring which mounts the blade to the handle. When the depressing force is released, the blade returns to its protected position. A mechanism is provided for locking the blade in its protected position.

While only a single preferred embodiment of the present invention has been disclosed for purposes of illustration, it is obvious that different various modifications and variations could be made thereto. For example, it is possible to mount the sheath for movement relative to the handle and fixably mount the blade so that it is necessary to move the sheath to expose the cutting edge. In addition, it is possible to provide the safety scalpel with a handle which is detachable from the blade and sheath assembly to permit replacement blades to be used with a single handle. It is intended to cover all of these variations and modifications which falls within the scope of the present invention as defined by the following claims:

I claim:

1. A scalpel comprising a handle, a blade having a cutting edge, means mounted on said handle for protecting said cutting edge, means for mounting said blade for movement relative to said protecting means from a protected position, wherein said cutting edge is within said protecting means, to an exposed position, wherein said cutting edge is exposed, means for biasing said blade toward said protected position, said protecting means having a cutaway portion exposing a part of said blade to permit access to said blade part for application force on said blade to move said blade toward said exposed position and further comprising means for locking said blade in said protected position, said locking means comprising means for preventing relative movement between said blade and said protecting means, said relative movement preventing means comprising a recess in said blade, and a part having a protrusion, said part being mounted for movement on said protecting means from a first position wherein said protrusion is situated within said recess and a second position wherein said protrusion is remote from said recess.

* * * * *